(12) United States Patent
Choe et al.

(10) Patent No.: US 9,926,358 B2
(45) Date of Patent: Mar. 27, 2018

(54) WATER-SOLUBLE EXPRESSION AND PURIFICATION METHOD OF HUMAN GCSF RECOMBINANT PROTEIN HAVING BIOLOGICAL ACTIVITIES

(71) Applicant: UNIVERSITY OF ULSAN FOUNDATION FOR INDUSTRY COOPERATION, Ulsan (KR)

(72) Inventors: Han Choe, Seoul (KR); Han Bong Ryu, Seoul (KR); Bich Hang Do, Hochiminh (VN)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 130 days.

(21) Appl. No.: 15/025,283

(22) PCT Filed: Sep. 24, 2014

(86) PCT No.: PCT/KR2014/008876
§ 371 (c)(1),
(2) Date: Mar. 28, 2016

(87) PCT Pub. No.: WO2015/046869
PCT Pub. Date: Apr. 2, 2015

(65) Prior Publication Data
US 2016/0215034 A1 Jul. 28, 2016

(30) Foreign Application Priority Data
Sep. 26, 2013 (KR) .................. 10-2013-0114432

(51) Int. Cl.
*C07K 14/535* (2006.01)
*C07K 2/00* (2006.01)

(52) U.S. Cl.
CPC .............. *C07K 14/535* (2013.01); *C07K 2/00* (2013.01); *C07K 2319/21* (2013.01)

(58) Field of Classification Search
None
See application file for complete search history.

(56) References Cited

U.S. PATENT DOCUMENTS

2009/0305351 A1 12/2009 Shin et al.
2011/0171168 A1 7/2011 Carter

FOREIGN PATENT DOCUMENTS

| KR | 10-2008-0039879 A | 5/2008 |
| KR | 10-2012-0057416 A | 6/2012 |
| WO | 2009-139784 A1 | 11/2009 |

OTHER PUBLICATIONS

International Search Report for PCT/KR2014/008876 dated Jan. 23, 2015 from Korean Intellectual Property Office.
Das, K. M. P. et al., Cloning, Soluble Expression and Purification of High Yield Recombinant hGMCSF in *Escherichia coli*., Int. J. Mol. Sci. 12(3): 2064-2076 (Mar. 2011).
Kim, C. W. et al., N-terminal domains of native multidomain proteins have the potential to assist de novo folding of their downstream domains in vivo by acting as solubility enhancers. Protein Science. 16(4): 635-643 (Mar. 2007).
Sarkar, C. A et al., Rational cytokine design for increased life time and enhanced potency using pH-activated "histidine switshing". Nature Biotechnology. 20(9): 908-913 (2002).

*Primary Examiner* — Suzanne M Noakes
(74) *Attorney, Agent, or Firm* — Revolution IP, PLLC (57) ABSTRACT

The present invention relates to a water-soluble expression and a purification method of a human granulocyte colony-stimulating factor (hGCSF) recombinant protein having biological activities using an N-terminal tag, and provides a recombinant expression vector containing a solubility enhancing tag and a hGCSF gene. In addition, provided are: a recombinant microorganism transformed with the recombinant expression vector; a method for producing a hGCSF recombinant protein (rhGCSF); and a rhGCSF produced by the production method.

9 Claims, 6 Drawing Sheets

WATER-SOLUBLE EXPRESSION AND PURIFICATION METHOD OF HUMAN GCSF RECOMBINANT PROTEIN HAVING BIOLOGICAL ACTIVITIES

CROSS REFERENCE TO PRIOR APPLICATIONS

This application is a National Stage Application of PCT International Patent Application No. PCT/KR2014/008876 filed on Sep. 24, 2014, under 35 U.S.C. § 371, which claims priority to Korean Patent Application No. 10-2013-0114432 filed on Sep. 26, 2013, which are all hereby incorporated by reference in their entirety.

TECHNICAL FIELD

The inventive concept relates to a water-soluble expression and a purification method of a human granulocyte colony-stimulating factor (hGCSF) recombinant protein having biological activities using an N-terminal tag.

BACKGROUND ART

A granulocyte colony-stimulating factor (GCSF), also known as pluripoietin, acts in hematopoiesis by controlling the production, differentiation, and function of the granulocytes that comprises 70% of white blood cells. The growth factor is secreted predominantly by macrophages, fibroblasts, and endothelials with several inflammatory stimuli such as interleukin-1β, tumor necrosis factor-alpha, and lipopolysaccharide. Clinically, human GCSF (hGCSF) has been approved for treatment of neutropenia, a disorder characterized by an extremely low number of neutrophils in blood. Usually cancer patients suffer from this leukopenia after radiotherapy or chemotherapy. Besides, GCSF has also expressed the neuroprotective property. Accordingly, the protein has been applied as a protective agent to mouse models of various neurodegenerative diseases, such as amyotrophic lateral sclerosis.

Initially the production of hGCSF was from a tumor cell line that continuously secreted hGCSF. When expressed in the methylotrophic yeast, Pichia Pastoris, the hormones were secreted in the soluble form but highly aggregated so that they had to be solubilized using high concentrations of denaturants such as guanidine hydrochloride or urea and subsequently refolded by removal of denaturants to be purified as the biologically active form. Many expression studies using bacteria such as Escherichia coli (E. coli) produced also inclusion bodies that is aggregation of overexpressed proteins in the cytoplasm. In many cases, the overall yield of biologically active protein from inclusion body is low. Alternatively, the protein was secreted to periplasm of E. coli, but the yield can be also low.

Although Korean Patent No. 2012-0057416 discloses polynucleotide for producing human G-CSF protein and a use thereof, there is no description about a tagging system such as a water-soluble expression of hGCSF and a hPDIb'a' domain for its separation according to an aspect of the inventive concept.

DETAILED DESCRIPTION OF THE INVENTIVE CONCEPT

Technical Problem

The inventive concept provides a recombinant expression vector including a solubility enhancing tag and a human granulocyte colony-stimulating factor (hGCSF) gene, and the inventive concept provides a recombinant microorganism transformed with the recombinant expression vector.

The inventive concept provides a method for producing a hGCSF recombinant protein (rhGCSF), and the inventive concept provides a rhGCSF produced by the method for producing a rhGCSF.

Technical Solution

According to an aspect of the inventive concept, there is provided a recombinant expression vector including a solubility enhancing tag and a human granulocyte colony-stimulating factor (hGCSF) gene.

According to another aspect of the inventive concept, there is provided a recombinant microorganism transformed with the recombinant expression vector.

According to another aspect of the inventive concept, there is provided a method of producing a hGCSF recombinant protein (rhGCSF).

According to another aspect of the inventive concept, there is provided a rhGCSF produced by using the method of producing a rhGCSF.

Advantageous Effects

As described herein, an aspect of the inventive concept relates to a water-soluble expression and a purification method of a human granulocyte colony-stimulating factor (hGCSF) recombinant protein using an N-terminal tag, and provides a method of separating and purifying a hGCSF protein with increased solubility and stability in E. coli by b'a'-domain tagging of a protein disulfide isomerase (PDI) at an N-terminal. The hGCSF protein thus obtained is expected to be used as a treatment for netropenia which occurs when the level of neutrophils in blood is extremely low.

BRIEF DESCRIPTION OF THE DRAWINGS

FIG. 3 illustrates purification of hGCSF from PDIb'a'-hGCSF. (A) A flowchart of a purification process. (B) PDIb'a'-hGCSF expressed from E. coli was analyzed by SDS-PAGE. Lane 5 indicates that hPDIb'a' is almost completely cleaved. M, molecular weight marker; lane 1, total cell proteins before IPTG induction as control; lane 2, total cell proteins after IPTG induction; lane 3, soluble fraction after cell sonication; lane 4, PDIb'a'-hGCSF fusion protein purified using His-trap HP column (59.1 kDa); lane 5, hPDIb'a' tag cleavage with TEV protease: hPDIb'a' (35.6 kDa) and hGCSF (18.8 kDa); lane 6, final purified hGCSF (18.8 kDa). (C) A chromatogram using His-trap HP column for purification of hGCSF after the cleavage. The hGCSF cleaved together with hPDIb'a is significantly distinctive by its size. (D) 10% SDS gel electrophoresis silver stained under reduced and nonreduced condition to confirm the final purity of the separated hGCSF. M, Molecular weight marker; R, reduced; NR, nonreduced.

FIG. 4 is related to purification of hGCSF from MBP-hGCSF. (A) A diagram of the hGCSF purification process. (B) The hGCSF was purified from E. coli by a combination of MBP affinity and IMAC chromatography. 10 ug of total proteins was loaded onto 10% Tris-tricine gel. M, molecular weight marker; lane 1, total cell proteins before IPTG induction as control; lane 2, total cell proteins after IPTG induction; lane 3, soluble fraction after cell sonication; lane 4, MBP-hGCSF fusion protein purified using MBP affinity column (63.3 kDa); lane5, His6-MBP tag cleavage with TEV protease: His6-MBP (40.3 kDa) and hGCSF (18.8 kDa); lane 6, final purified hGCSF (18.8 kDa). (C) An image of silver stained 10% SDS gel electrophoresis of purified hGCSF in reduced condition for the confirmation of its final purity. M, molecular weight marker; lane 1, final purified hGCSF. (D) A result of purification of hGCSF monomer by gel filtration. This also shows Superdex 200 16/60 chromatogram of hGCSF after 2nd purification step. (E) A silver staining result of purified hGCSF. M, Molecular weight marker; lanes 1 and 2, hGCSF was reduced depending on the presence of 10 mM DTT.

BEST MODE

The present inventors have developed a method solubly expressing human granulocyte colony-stimulating factor (hGCSF) protein having biological activities in the cytoplasm of E. coli. Seven N-terminal fusion tags, hexahistidine (His6), thioredoxin (Trx), glutathione S-transferase (GST), maltose binding protein (MBP), N-utilization substance protein A (NusA), human protein disulfide bond isomerase (hPDI), and b'a' domain of hPDI (hPDIb'a'), were tested for soluble overexpression of hGCSF. It was confirmed that four tag proteins, MBP, NusA, hPDI, and hPDIb'a' increased the solubility of hGCSF significantly at 30° C., and the activity of hGCSF was measured using myeloid leukemia M-NFS 60 cells, thereby completing the present invention.

The present invention provides a recombinant expression vector including a solubility enhancing tag and a hGCSF gene.

According to an embodiment of the present invention, the solubility enhancing tag may be any material capable of expressing a hGCSF recombinant protein in the soluble form. For example, the solubility enhancing tag may be one selected from hexahistidine (His6), thioredoxin (Trx), glutathione S-transferase (GST), maltose binding protein (MBP), N-utilization substance protein A (NusA), human protein disulfide isomerase (hPDI), and b'a' domain of hPDI (hPDIb'a').

Figure 1:
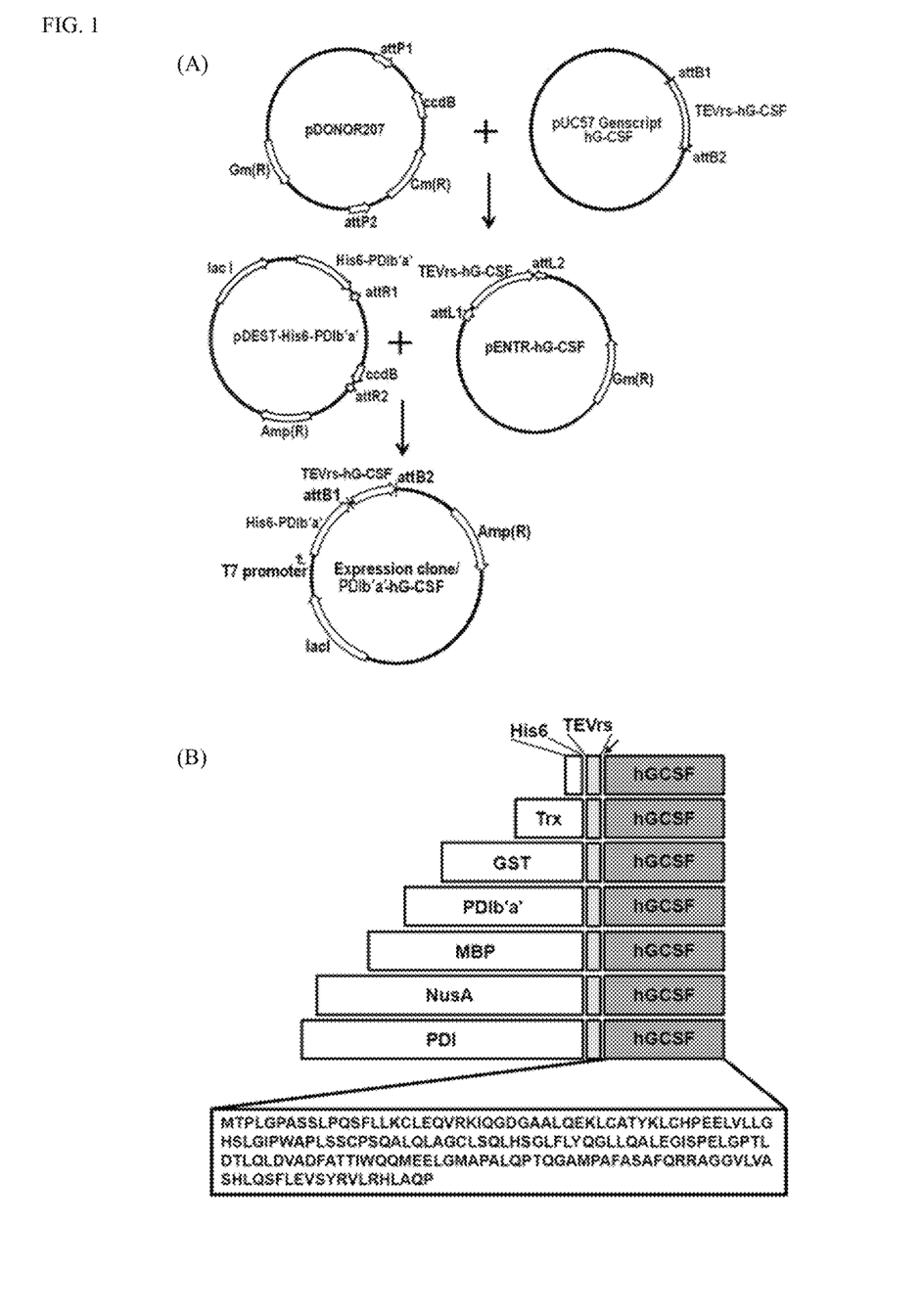
FIG. 1 illustrates a preparation process of a PDIb'a'-hGCSF expression vector and is a schematic view of a domain structure. (A) Vector map of PDIb'a'-hGCSF. Expression of fusion proteins in E. coli is controlled by the IPTG-inducible T7 promoter, and the selection marker is ampicillin. (B) Schematic structure of 7 different fusion proteins (His6-, Trx-, GST-, PDIb'a'-, MBP-, PDI-, and NusA-hGCSF); hGCSF amino acid sequence (SEQ ID NO: 7) is also presented.

In particular, the hGCSF gene is a nucleic acid sequence represented by SEQ ID NO: 1, the Trx gene is a nucleic acid sequence represented by SEQ ID NO: 2, the GST gene is a nucleic acid sequence represented by SEQ ID NO: 3, the NusA gene is a nucleic acid sequence represented by SEQ ID NO: 4, and the hPDIb'a' gene is a nucleic acid sequence represented by SEQ ID NO: 5. The hPDIb'a' gene is the same with the partially removed hPDI gene, and thus the hPDI gene is represented by SEQ ID NO: 6. Also, hGCSF amino acid sequence is represented by SEQ ID NO: 7. Particularly, the recombinant expression vector is characterized in having a cleavage map shown in FIG. 1A.

As used herein, the term "vector" refers to an autonomously replicating DNA molecule that is used to deliver a clone gene (or a fragment of a clone DNA)

As used herein, the term "expression vector" denotes a recombinant DNA molecule including a desired coding sequence and other appropriate nucleic acid sequences, which are essential for expression of the operatively-linked coding sequence in a particular host organism. The expression vector may preferably include at least one selective marker. The marker is a nucleic acid sequence having characteristics that may be generally selected by a chemical method, and all genes that allows distinction of transformed cells from non-transformed cells correspond the marker. Examples of the marker may include antibiotic resistance genes, such as ampicilin, kanamycin, G418, bleomycin, hygromycin, and chloramphenicol, but the examples are not limited thereto, and any gene may be appropriately selected by those of ordinary skill in the art.

The Gateway Vector system used herein is constituted with an entry vector and a destination vector, and the entry vector is a vector having attL1 and attL2 at both ends of a destination gene, and the destination vector is a vector including attR1 and attR2. In terms of the entry vector and the destination vector, attR1 and attR2 of the destination vector generate LR reaction with attL1 and attL2 of the entry vector by a recombinant enzyme. During this process, the destination gene included in the entry vector is transferred to the target vector, and attR1 and attR2 are substituted with attB1 and attB2 sequences.

Also, the present invention provides a recombinant microorganism transformed with the recombinant expression vector. In particular, the microorganism is E. coli, or, for example, E. coli BL21(DE3).

Also, the present invention provides a recombinant microorganism, in which a gene construct including a solubility enhancing tag and a hGCSF gene is inserted in a chromosome of a host cell. It would have been obvious to those of ordinary skill in the art that the effects produced by inserting the gene to a genome chromosome of a host cell are the same with the case when the recombinant vector is introduced to a host cell as described above.

In the present invention, a generally known gene modification method may be used to insert the gene to a chromosome of a host cell, and, for example, a method using a retrovirus vector, an adenovirus vector, an adeno-associated virus vector, a herpes simplex virus vector, a poxvirus vector, a lentivirus vector, or a non-viral vector may be used.

Also, the present invention provides a method of producing a hGCSF recombinant protein (rhGCSF), wherein the method includes culturing the recombinant microorganism to express a solubility enhancing tag-hGCSF recombinant protein; removing a solubility enhancing tag from the expressed solubility enhancing tag-hGCSF recombinant protein; and collecting a hGCSF recombinant protein from which the solubility enhancing tag is removed.

Although, a tobacco etch virus (TEV) protease is used in an embodiment of the present invention, examples of the protease may include factor Xa protease, thrombin, enterokinase, ubiquitin-specific protease, furin, genease I, or proteinase K that may be generally used in the art, and the examples of the protease is not limited thereto.

Also, the present invention provides a rhGCSF produced by using the production method.

Genetically engineering technology used herein may be referred to Sambrook, et al. Molecular Cloning, A Laboratory Manual, Cold Spring Harbor laboratory Press, Cold Spring Harbor, N. Y.(2001) and Frederick M. Ausubel et al., Current protocols in molecular biology volume 1,2,3, John Wiley & Sons, Inc.(1994).

Mode of the Inventive Concept

Hereinafter, one or more embodiments of the present invention will be described in detail with reference to the following examples. However, these examples are not intended to limit the scope of the present invention.

EXAMPLE 1

Manufacture and Expression of Expression Vector

A hGCSF gene (NCBI Reference Sequence: NP_757373) was codon optimized and flanked with attB$_1$ site (5'-GGGGACAAGTTTGTACAAAAAAGCAGGCTTC-3'; SEQ ID NO: 9), TEV protease recognition site (TEVrs; ENLYFQG), and attB$_2$ (5'-ACCCAGCTTTCTTGTA-CAAAGTGGTCCCC-3'; SEQ ID NO: 10). The DNA was synthesized and subcloned into plasmid pUC57 (Genscript, New Jersey, USA). The plasmid containing hGCSF gene was recombined with pDONOR207 (Invitrogen, Carlsbad, Calif., USA) to produce the entry vector pENTR-hGCSF. Subsequently, LR recombination cloning between pENTR-hGCSF and the seven destination vectors, pDEST-HGWA, pDEST-HXGWA, pDEST-HGGWA, pDEST-HMGWA, pDEST-HNGWA, pDEST-PDI, and pDEST-PDIb'a', was applied to produce expression vectors containing hGCSF and the tags. The sequences of the expression plasmids were confirmed by DNA sequencing (Macrogen, Daej eon, Korea) and transformed to *E.coli* BL21 (DE3).

In order to express hGCSF in the soluble form in the cytoplasm of *E. coli*, seven tag genes, His6, Trx, GST, PDI b'a', MBP, PDI and NusA, were fused to N-terminus of hGCSF sequence as shown in FIG. 1. TEVrs was inserted between the tags and hGCSF to separate them during purification.

Figure 2:
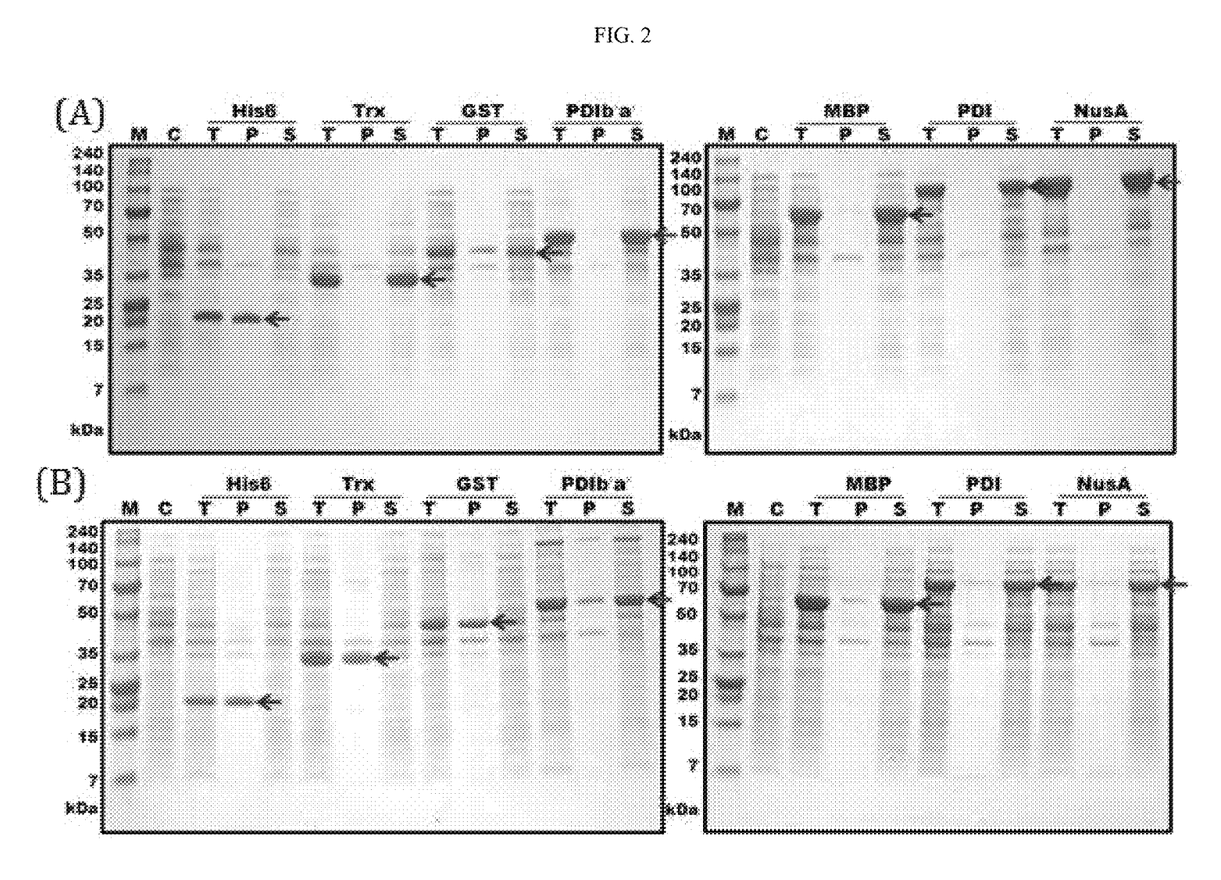
FIG. 2 shows the results of E. coli expression analysis of hGCSF fused with seven tags by SDS-PAGE gel. Protein expression was induced with 1 mM IPTG at 18° C. (A) and 30° C. (B). After sonication, 20 ug of total proteins were loaded onto 10% Tris-tricine gel. Arrows indicate hCCL2 proteins fused with each tags. M, molecular weight size marker; C, total cell proteins before IPTG induction as control; T, total cell proteins after IPTG induction; P, proteins in the pellet after sonication; S, proteins in supernatant after sonication.

The cells were grown in 2 mL LB broth with 50 μg/mL ampicillin and incubated at 37° C., 200 rpm. When the OD$_{600}$ was approximately 0.4 to 0.6, 1 mM isopropyl-β-D-thiogalactoside (IPTG) was supplied to induce the expression of hGCSF fusion proteins. The cells were harvested after incubation for 5 hours at 30° C. and for 12 hours at 18° C., respectively (see FIG. 2 and Table 1). The expression levels of hGCSF with all the tags at two expression temperatures were between 33 to 68%, with higher expression level at 18° C. The solubility varied depending on the tags and the expression temperature. Four tag proteins, MBP, NusA, PDI, and PDIb'a', increased the solubility of hGCSF significantly at 30° C. (see FIG. 2A and Table 1). Also, lowering expression temperature to 18° C. increased the solubility of Trx-hGCSF and GST-hGCSF (see FIG. 2B and Table 1). His6-hGCSF was insoluble at both expression temperatures. Based on solubility and the size of the tag proteins, the present inventors selected two fusion proteins, PDIb'a'-hGCSF and MBP-hGCSF for further study.

TABLE 1

Expression level and solubility of hGCSF having various N-terminal tags

| | Tag | Tag size (kDa) | Fusion protein size (kDa) | Expression (%) 18° C. | Expression (%) 30° C. | Solubility (%) 18° C. | Solubility (%) 30° C. |
|---|---|---|---|---|---|---|---|
| hGCSF (18.8 kDa) | His6 | 0.8 | 23.5 | 43.8 | 33.6 | — | — |
| | Trx | 11.8 | 35.3 | 61.4 | 48.8 | 98.3 | 5.0 |
| | GST | 25.7 | 49.2 | 41.3 | 40.0 | 78.4 | 3.2 |
| | PDIb'a' | 35.6 | 59.1 | 66.3 | 42.2 | 96.0 | 73.5 |
| | MBP | 40.3 | 63.8 | 61.4 | 58.4 | 96.5 | 88.1 |
| | PDI | 55.1 | 78.7 | 55.6 | 43.8 | 98.1 | 89.3 |
| | NusA | 54.9 | 78.4 | 68.0 | 44.8 | 97.5 | 89.5 |

EXAMPLE 2

Separation and Purification of Recombinant hGCSF

1. Separation and purification of hGCSF from hPDIb'a'-hGCSF

In order to express hPDIb'a'-hGCSF, a 3×5 mL HisTrap HP column (GE Healthcare, Piscataway, N.J., USA) was used in the first step to separate this fusion protein. After equilibrating the column by using a binding buffer, the column was fed with a lysate solution, followed by the flow through of a washing buffer (50 mM Tris-HCl, pH 8.0, 500 mM NaCl, 100 mM imidazole, 5% glycerol (v/v)) to remove all unspecific bindings. The hPDIb'a'-hGCSF was eluted using a buffer containing 500 mM imidazole (50 mM Tris-HCl, pH 8.0, 500 mM NaCl, 500 mM imidazole, 5% glycerol (v/v)) and exchanged with a free NaCl buffer (50 mM Tris-HCl, pH 8.0, 5% glycerol (v/v)) through dialysis membrane (Viskase Corpration, Illinois, USA). Eluted sample was cleaved by TEV protease with the ratio 1:20 of protein: TEV protease at 18° C. for 12 hours. Next, the cleaved solution was spent during a buffer exchanging process and added to a HisTrap binding buffer (50mM Tris-HCl, pH 8.0, 500 mM NaCl, 5% glycerol (v/v)) through a 10 kDa dialysis membrane (Viskase Corpration, Illinois, USA). All treated sample was loaded onto 2×5 mL IMAC using a pre-packed HisTrap HP column (GE Healthcare, Piscataway, N.J., USA) entirely filled with a binding buffer (50 mM Tris-HCl, pH 8.0, 500 mM NaCl, 5% glycerol (v/v)). Unlike other proteins in the solution, hGCSF had low affinity to Ni resin and easily left HisTrap column by 50 mM imidazole washing (50 mM Tris-HCl, pH 8.0, 500 mM NaCl, 5% glycerol, 50 mM imidazole (v/v)). Base on the chromatogram, hGCSF monomer was confirmed by 10% Tris-tricine SDS-PAGE analysis under reduced and non-reduced condition.

2. Separation and Purification of hGCSF from MBP-hGCSF

The MBP-hGCSF clone was pre-culture before scaling up to 500 mL with the induction of 1 mM IPTG at 18° C. for 12 hours to overexpress the MBP-hGCSF fusion protein. The centrifugation at 3,500 rpm for 30 minutes was achieved to harvest the cultured cells. Subsequently, the collected pellet was resuspended in 100 mL MBP binding buffer (50 mM Tris-HCl, pH 8.0, 0.5 mM EDTA, 200 mM NaCl, 5% glycerol (v/v)) and sonicated in cold until the solution was completely transparent, followed by centrifuging at 15,000 rpm for 20 min. The lysate after the centrifuging and filtering was applied onto 2×5 mL MBP Trap HP (GE Healthcare, Piscataway, N.J., USA) using AKTA Prime Plus machine (GE life science, NF, USA) equilibrated with the MBP binding buffer. Non-specific binding proteins were washed away by using a binding buffer and MBP-hGCSF was eluted by using a buffer containing maltose (50 mM Tris-HCl, pH 8.0, 0.5 mM EDTA, 200 mM NaCl, 5% glycerol, 10 mM maltose monohydrate (v/v)). Base on the chromatogram, MBP-hGCSF was pooled and confirmed by 10% Tris-tricine SDS-PAGE analysis. The eluted sample was diluted until the final concentration of NaCl was 50 mM, and then a TEV treating process and a purification process of the cleaved hGCSF were performed in the same manner as in the method of cleaving hGCSF from hPDIb'a'-hGCSF. In order to divide a hGCSF monomer from a polymer as well as to exchange the buffer of hGCSF with PBS buffer, the hGCSF pooled from the washing process was loaded onto gel filtration superdex 200 16/60 column (GE Healthcare, Piscataway, N.J., USA) in PBS buffer (137 mM NaCl, 2.7 mM KCl, 8 mM $Na_2HPO_4$, 1.4 mM $KH_2PO_4$, 5% glycerol (v/v)). Base on the chromatogram, hGCSF monomer was confirmed by 10% Tris-tricine SDS-PAGE analysis under reduced and non-reduced condition.

3. SDS-PAGE Analysis and Silver Staining

The presence of protein was visible on 10% Tris-tricine gel with coomassie blue R-250 (AMRESCO, Solon, Ohio, USA) for developing protein bands. The expression, solubility, and purity were quantified by ImageJ program.

For silver staining, polyacrylamide gel was placed onto Fixative Enhancer Solution for 20 min, followed by rinsing with distilled water to increase the sensitivity and contrast staining. The reaction of staining and developing was carried out by adding a silver complex solution, a reduction moderator solution, and an image development reagent, respectively, (Bio-Rad Laboratories, Hercules, Calif., USA) and stopped by using a 5% acetic acid solution.

4. Result (1) Purification of hGCSF from PDIb'a'-hGCSF

Figure 3:
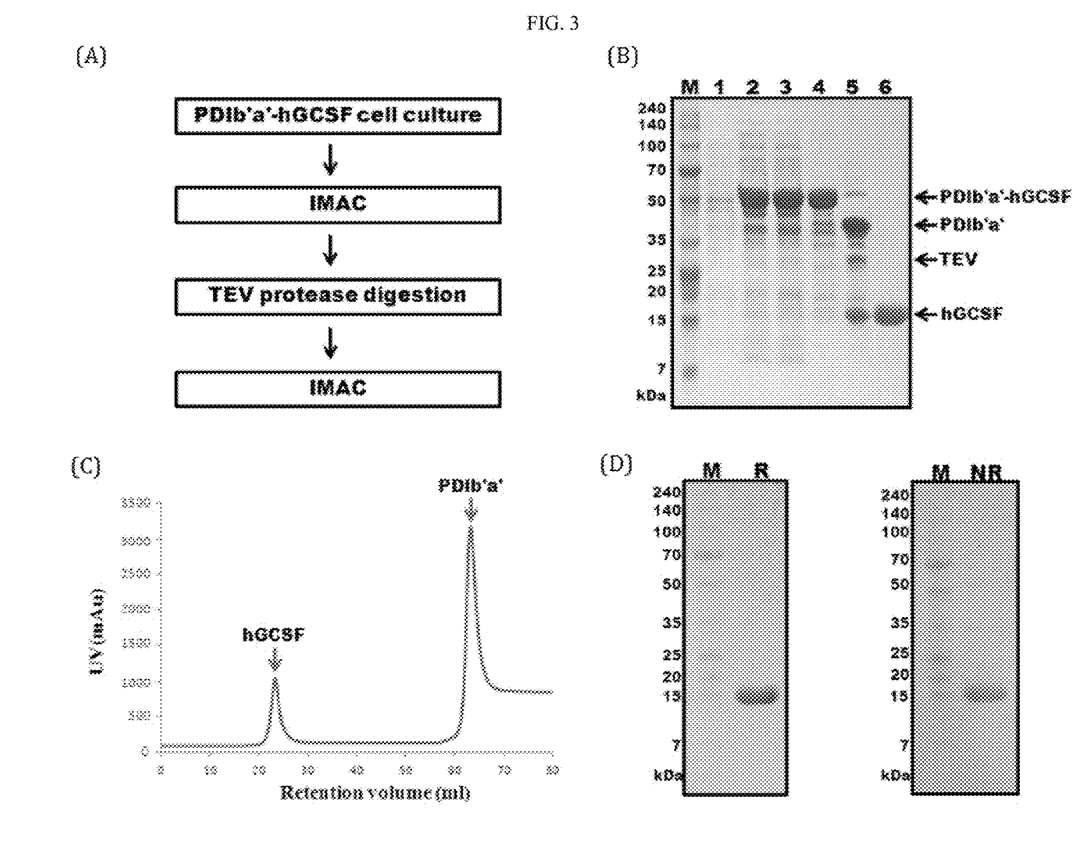

The purification of hGCSF from PDI-hBMP4 was performed with two times of IMAC and final GPC (see FIG. 3A). IMAC was possible because all of the N-terminal tags used herein had a His6 tag. The cell containing the plasmid of PDIb'a'-hGCSF was induced with IPTG and then collected (see FIG. 3B, lane 2). The cell was lysed and centrifuged to harvest the supernatant (see FIG. 3B, lane 3). Then the supernatant was loaded to a Ni column and the bonded protein was eluted after the washing process (see FIG. 3B, lane 4). Most of the other proteins were removed in this process, but some minor contaminant bands still remained. The present inventors went TEV protease digestion despite in the presence of other protein bands. Most of PDIb'a'-hGCSF was cleaved by TEV protease (see FIG. 3B, lane 5). To remove the PDIb'a' tag, the uncleaved PDIb'a'-hGCSF, and TEV protease, a second His-trap HP column was used. The cleaved hGCSF was weakly bound to the Ni column and eluted by 50 mM imidazole. To remove the remaining impurities, the samples were loaded to Superdex gel filtration column (see FIG. 3C). The hGCSF was completely separated from others, and pure hBMP4 was obtained (see FIG. 3B, lane 6). To test the purity, a silver staining was carried out with the purified hGCSF in reduced condition and the result showed that indeed the hGCSF was pure (see FIG. 3D). About 11.3 mg of pure hGCSF was obtained from 1 L of cell culture (see Table 2).

(2) Purification of hGCSF from MBP-hGCSF

Figure 4:
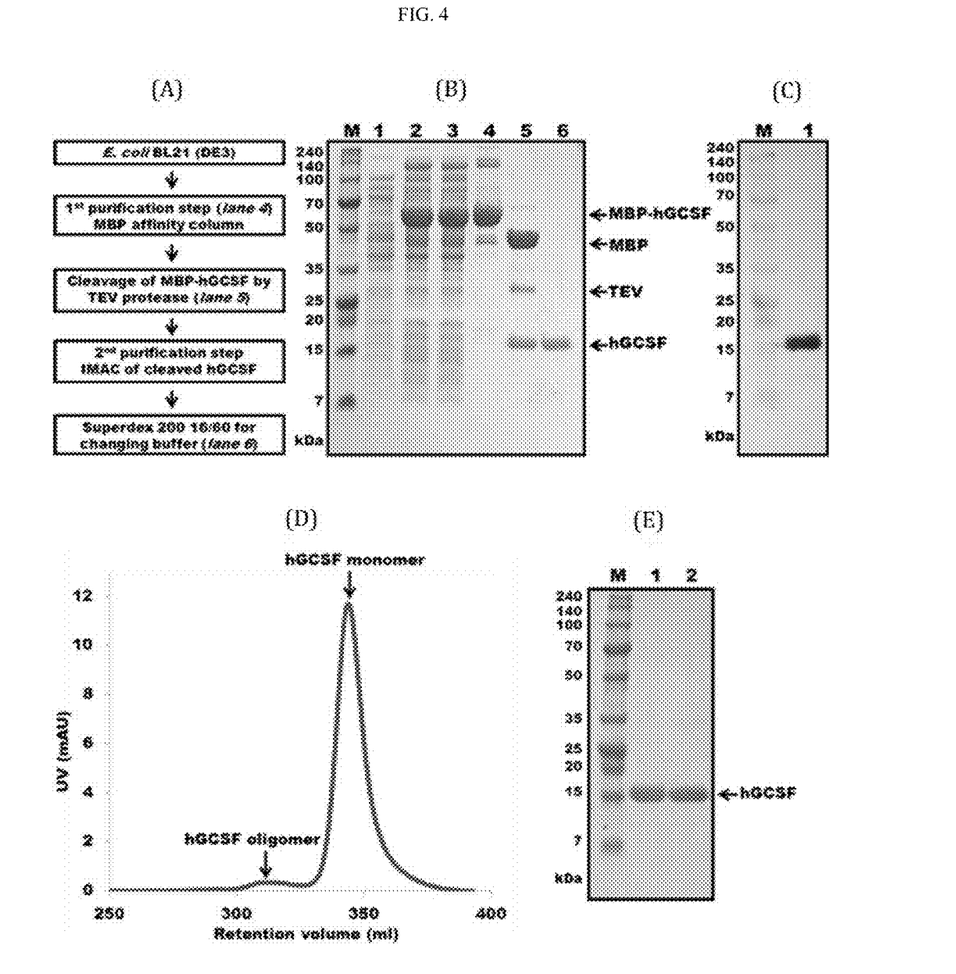

FIG. 4A shows an overall purification process of hGCSF from MBP-hGCSF. In the hGCSF purification process, first step of MBP chromatography distributed to the dissociation of about 80% of MBP-hGCSF fusion protein from a protein mixture (see FIG. 4B, lane 4). Subsequently, MBP-hGCSF was treated with a TEV protease to perform cleavage at a low concentration (TEV:target protein (1:20)) and released hGCSF alone (FIG. 4B, lane 5). After TEV cleavage, a mixture with hGCSF polymers (in which hGCSF monomers cover approximately 92%) underwent a washing step with 50 mM of imidazole through Ni NTA chromatography to obtain the hGCSF monomers from the mixture. In the consequence of separating hGCSF monomer by using Superdex 200, most protein eluted at 330 to 370 mL of retention volume was hGCSF monomers (see FIG. 4B, lane 6 and FIG. 4D). The hGCSF monomer was confirmed by SDS-PAGE analysis in the reducing and non-reducing condition which expressed about 2% of remaining dimer in the final product (see FIG. 4E). The result of silver staining confirmed that the purity of hGCSF was approximately 99.8% (see FIG. 4C). As a result, about 10.2 mg of purified hGCSF was obtained from 1 L of the cell culture (see Table 2).

TABLE 2

| | Purification process | | | | | | | |
|---|---|---|---|---|---|---|---|---|
| | Purification of hGCSF from PDIb'a'-hGCSF | | | | Purification of hGCSF from MBP-hGCSF | | | |
| Purification step | Total protein (mg) | Purity (%) | hGCSF (mg) | Yield (%) | Weight (mg) | Purity (%) | hGCSF (mg) | Yield (%) |
| Cell weight | 1500 | — | — | — | 1500 | — | — | — |
| Supernatant | 140 | 69.1 | 30.8 | — | 118.8 | 75.9 | 26.6 | — |
| $1^{st}$ Chromatography (IMAC/MBP) | 71.5 | 73.3 | 16.7 | 54 | 79.8 | 88 | 20.7 | 77.8 |
| $2^{nd}$ Chromatography | 11.4 | 99 | 11.3 | 36.7 | 10.3 | 99 | 10.2 | 38.3 |

EXAMPLE 3 hGCSF Endotoxin Assay

In order to eliminate the endotoxin from the purified hGCSF solution, Triton X-114 (Sigma-Aldrich, St. Louis, Mo., USA) was used was at the final concentration of 1% and treated at 4° C. for 30 minutes. Triton X-114 was accumulated after reacting with the sample at room temperature and removed by centrifugation at 12,000 rpm for 10 minutes.

Endpoint Chromogenic Limulus Amebocyte Lysate (LAL) test (Lonza, Basel, Switzerland) was applied to measure the remained endotoxin in the target solution. LAL and hGCSF sample was mixed and incubated at 37° C. for 10 minutes before a substrate was added. And then, a stopping agent (25% v/v glacial acetic acid) was added to mixture. The pNA released therefrom was evaluated by using a spectrophotometer in a range of 405 to 410 nm.

The remaining endotoxin amount in the solution was lower than 0.1 EU/µg after the treatment of Triton X-114. This value was satisfactory for a purified protein from *E. coli* compared to the endotoxin of commercial hGCSF (<1 EU/µg).

EXAMPLE 4

Confirmation of Recombinant hGCSF by MALDI-TOF MS Analysis

To identify hGCSF and confirm a disulfide bond, MALDI-TOF MS analysis was carried out. Under reduced or non-reduced condition depending on with or without 10 mM DTT, hGCSF was precipitated by tricloroacetic acid (TCA) and treated with 50 mM IAA in IA buffer (0.5 M Tris-HCl, pH 8.0, 5% glycerol (v/v), 100 mM NaCl, 1 mM EDTA, 1% SDS) for 1 hour in dark. After running SDS-PAGE, the band associated with hGCSF was cut from gel and cleaved by chemotrypsin (Promega, Madison, Wis., USA) at 37° C. overnight. The α-Cyano-4-hydroxycinnamic acid (CHCA) was used as a matrix, and the MALDI-TOF MS process was performed by using Voyager-DE™ STR (Applied Biosystems, South San Francisco, Calif., USA) and 4700 MALDI TOF/TOF™ Analyzer (AB Sciex, Framingham, Mass., USA). A weight of the peptide was analyzed by Data Explorer™ software (Applied Biosystems, South San Francisco, Calif., USA).

Figure 5:
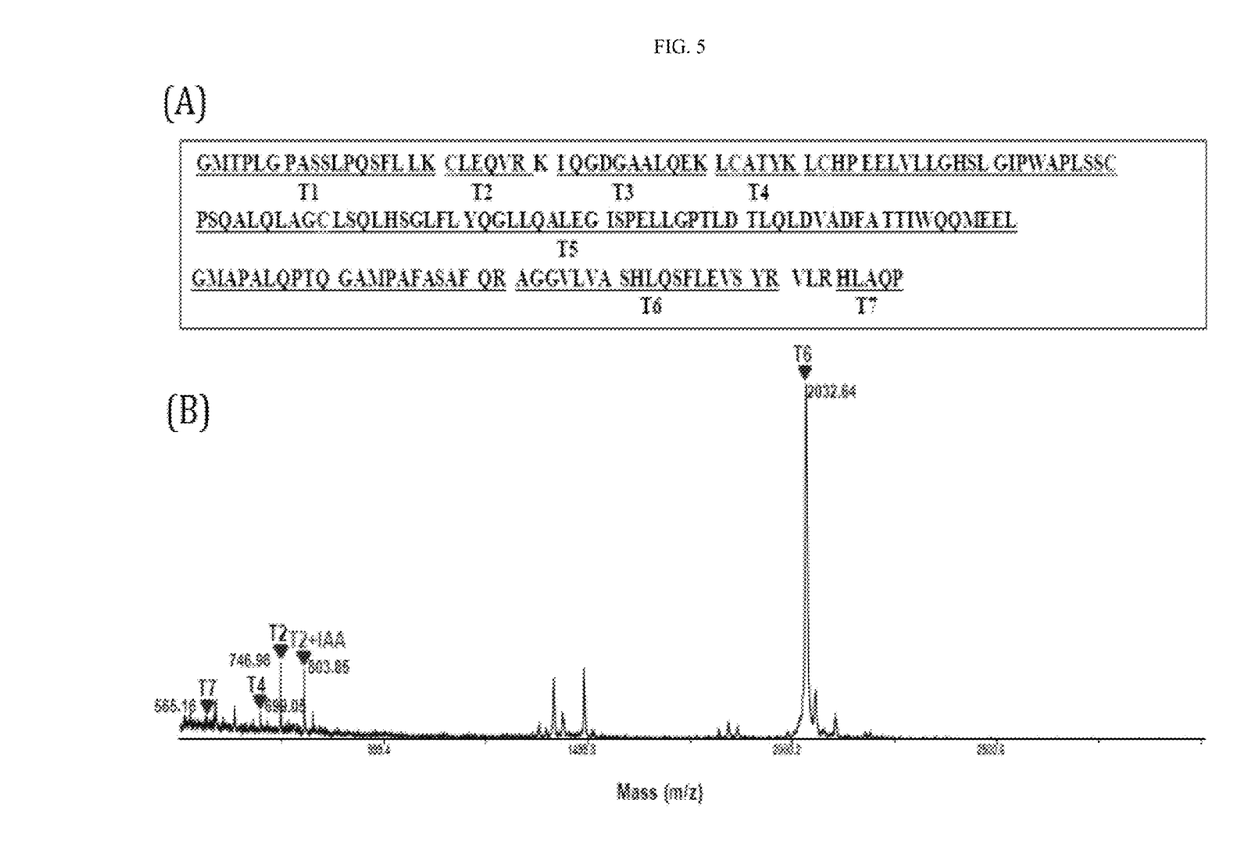
FIG. 5 shows the result of MALDI-TOF MS analysis performed on hGCSF. (A) A trypsin cleaving peptide map of hGCSF (aa) represented by SEQ ID NO: 8. (B) The result of MALDI-TOF MS analysis performed on hGCSF purified under reduced condition.

In order to confirm the separated hGCSF, MALDI-TOF MS analysis was carried out under reduced condition. The results of MALDI-TOF MS analysis performed on the separated hGCSF showed that most of a weight of the trypsin cleavable peptide is related to hGCSF (see FIG. 5).

In was confirmed that a T2 peptide fragment, to which C19 belongs, among five cysteine remaining groups of hGCSF is freed by bonding with iodoacetamide under the reduced condition (see FIG. 5B).

EXAMPLE 5

Measurement of Biological Activities of Purified hGCSF

1. M-NFS60 Cell Culture

M-NFS60 cell line, provided by Dr. Kyung-Woon Kim, was grown in a medium composed of RPMI-1640 medium (GIBCO Invitrogen, Calif., USA), 10% fetal bovine serum (FBS), 1× penicillin streptomycin (GIBCO Invitrogen, Calif., USA), and 0.05 mM β-mercaptoethanol. Cells were maintained at 37° C. in 5% $CO_2$.

2. Colorimetric Assay

Bioassay of purified hGCSF on M-NFS60 cells was based on the WST-1 (2-(4-Iodophenyl)-3-(4-nitrophenyl)-5-(2,4-disulfophenyl)-2H-tetrazolium, monosodium salt) assay (Roche, Ind., USA). The cultured cells were inoculated into a 96-well plate containing culturing medium at a density of $3 \times 10^4$ cells per well. Simultaneously, hGCSF at different concentrations of hGCSF (0.001, 0.005, 0.01, 0.05, 0.1, 0.05, 1, 5, or 10 ng/mL) was added to final volume of 100 µl in each well to survey the influence of hGCSF on M-NFS60 cells. After 72 hours of incubation, 10 µl of Cell Proliferation Reagent WST-1 was added thereto, and incubated in dark at 37° C. for 1 hour. Finally, the optical density at 450 nm of wavelength was measured by ELISA plate reader.

3. Results

Figure 6:
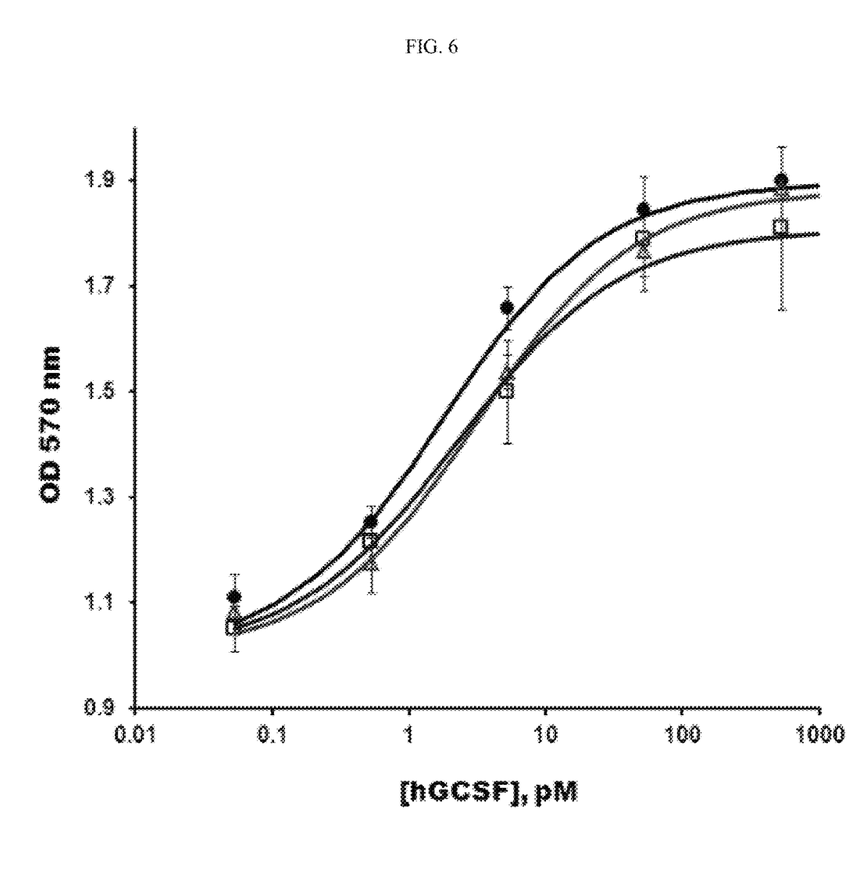
FIG. 6 shows biological activities of purified hGCSF with respect to M-NFS 60 cells. The purified hGCSF at various concentrations was cultured together with myeloid leukemia M-NFS 60 cell for 72 hours. •: commercial hGCSF, A: hGCSF purified from MBP-hGCSF,□: hGCSF purified from PDIb'a' -hGCSF.

In order to confirm biological activities of the separated hGCSF, amplification of myeloid leukemia M-NFS 60 cells was measured by WST-1 assay. As a result, the hGCSF separated from PDIb'a' or MBP tags had biological activities similar to those of commercial hGCSF (see FIG. 6). The activities increased geometrically from 1 pM, and the maximum value was around 80 pM. $EC_{50}$ of the commercial hGCSF was 1.62±0.19 pM, $EC_{50}$ of the hGCSF separated from PDIb'a' tag was 2.78±0.27 pM, and $EC_{50}$ of the hGCSF purified from MBP tag was 3.49±0.54 pM (Hill coefficients thereof are 0.73±0.21, 0.71±0.29, and 0.67±0.21, respectively).

The invention claimed is:

1. A recombinant expression vector comprising:
   a gene encoding a solubility enhancing tag; and
   a human granulocyte colony-stimulating factor (hGCSF) gene comprising the nucleic acid sequence represented by SEQ ID NO: 1.

2. The recombinant expression vector of claim 1, wherein the solubility enhancing tag is one selected from the group consisting of thioredoxin (Trx), glutatione S-transferase (GST), N-utilization substance protein A (NusA), and a human protein disulfide isomerase b'a' domain (hPDIb'a').

3. The recombinant expression vector of claim 2, wherein the Trx gene is a nucleic acid sequence represented by SEQ ID NO: 2, the GST gene is a nucleic acid sequence represented by SEQ ID NO: 3, the NusA gene is a nucleic acid sequence represented by SEQ ID NO: 4, and the hPDIb'a' gene is a nucleic acid sequence represented by SEQ ID NO: 5.

4. The recombinant expression vector of claim 1, wherein the recombinant expression vector has the final cleavage map shown in (A) of FIG. 1.

5. A recombinant microorganism transformed with the recombinant expression vector of claim 1.

6. The recombinant microorganism of claim 5, wherein the microorganism is *E. coli*.

7. The recombinant microorganism of claim 6, wherein the *E. coli* is BL21(DE3).

8. A method of producing a hGCSF recombinant protein (rhGCSF), the method comprising:
   culturing the recombinant microorganism of claim 5 to express a solubility enhancing tag-hGCSF recombinant protein;
   removing a solubility enhancing tag from the expressed solubility enhancing tag-hGCSF recombinant protein; and
   collecting a hGCSF recombinant protein from which the solubility enhancing tag is removed.

9. The method of claim 8, wherein the solubility enhancing tag is one selected from the group consisting of thioredoxin (Trx), glutatione S-transferase (GST), N-utilization substance protein A (NusA), and a human protein disulfide isomerase b'a' domain (hPDIb'a').

* * * * *

SEQUENCE LISTING

```
<160> NUMBER OF SEQ ID NOS: 10

<210> SEQ ID NO 1
<211> LENGTH: 525
<212> TYPE: DNA
<213> ORGANISM: Homo sapiens

<400> SEQUENCE: 1 atgacccgc tgggcccggc gtcttctctg ccgcaatcgt tcctgctgaa atgcctggaa      60
caggttcgta agattcaagg cgatggtgcg gccctgcagg aaaaactgtg cgccacctat     120
aagctgtgtc atccggaaga actggtcctg ctgggtcaca gcctgggtat cccgtgggca     180
ccgctgagct cttgcccgtc tcaggccctg caactggcag gctgtctgag tcagctgcat     240
tccggcctgt ttctgtacca gggtctgctg caagcgctgg aaggcattag tccggaactg     300
ggtccgaccc tggacacgct gcagctggat gtggctgact tcgcgaccac gatctggcag     360
caaatggaag aactgggtat ggcaccggct ctgcagccga cgcaaggtgc tatgccggcg     420
```

| | |
|---|---|
| tttgcatccg cattccagcg tcgcgctggc ggtgtgctgg ttgcgtcaca tctgcaatcg | 480 |
| tttctggaag tcagctatcg tgtgctgcgc cacctggccc agccg | 525 |

<210> SEQ ID NO 2
<211> LENGTH: 324
<212> TYPE: DNA
<213> ORGANISM: Homo sapiens

<400> SEQUENCE: 2

| | |
|---|---|
| agcgataaaa ttattcacct gactgacgac agttttgaca cggatgtact caaagcggac | 60 |
| ggggcgatcc tcgtcgattt ctgggcagag tggtgcggtc cgtgcaaaat gatcgccccg | 120 |
| attctggatg aaatcgctga cgaatatcag ggcaaactga ccgttgcaaa actgaacatc | 180 |
| gatcaaaacc ctggcactgc gccgaaatat ggcatccgtg gtatcccgac tctgctgctg | 240 |
| ttcaaaaacg gtgaagtggc ggcaaccaaa gtgggtgcac tgtctaaagg tcagttgaaa | 300 |
| gagttcctcg acgctaacct ggcc | 324 |

<210> SEQ ID NO 3
<211> LENGTH: 668
<212> TYPE: DNA
<213> ORGANISM: Homo sapiens

<400> SEQUENCE: 3

| | |
|---|---|
| atgtccccta tactaggtta ttggaaaatt aagggccttg tgcaacccac tcgacttctt | 60 |
| ttggaatatc ttgaagaaaa atatgaagag catttgtatg agcgcgatga aggtgataaa | 120 |
| tggcgaaaca aaaagtttga attgggtttg gagtttccca atcttcctta ttatattgat | 180 |
| ggtgatgtta aattaacaca gtctatggcc atcatacgtt atatagctga caagcacaac | 240 |
| atgttgggtg gttgtccaaa agagcgtgca gagatttcaa tgcttgaagg agcggttttg | 300 |
| gatattagat acggtgtttc gagaattgca tatagtaaag actttgaaac tctcaaagtt | 360 |
| gattttctta gcaagctacc tgaaatgctg aaaatgttcg aagatcgttt atgtcataaa | 420 |
| acatatttaa atggtgatca tgtaacccat cctgacttca tgttgtatga cgctcttgat | 480 |
| gttgttttat acatggaccc aatgtgcctg gatgcgttcc caaaattagt ttgttttaaa | 540 |
| aaacgtattg aagctatccc acaaattgat aagtacttga atccagcaa gtatatagca | 600 |
| tggcctttgc agggctggca agccacgttt ggtggtggcg accatcctcc aaaatcggat | 660 |
| ctggttcc | 668 |

<210> SEQ ID NO 4
<211> LENGTH: 1482
<212> TYPE: DNA
<213> ORGANISM: Homo sapiens

<400> SEQUENCE: 4

| | |
|---|---|
| aacaaagaaa ttttggctgt agttgaagcc gtatccaatg aaaaggcgct acctcgcgag | 60 |
| aagattttcg aagcattgga aagcgcgctg gcgacagcaa caaagaaaaa atatgaacaa | 120 |
| gagatcgacg tccgcgtaca gatcgatcgc aaaagcggtg attttgacac tttccgtcgc | 180 |
| tggttagttg ttgatgaagt cacccagccg accaaggaaa tcacccttga gccgcacgt | 240 |
| tatgaagatg aaagcctgaa cctgggcgat tacgttgaag atcagattga gtctgttacc | 300 |
| tttgaccgta tcactaccca gacggcaaaa caggttatcg tgcagaaagt gcgtgaagcc | 360 |
| gaacgtgcga tggtggttga tcagttccgt gaacacgaag gtgaaatcat caccggcgtg | 420 |

| | |
|---|---|
| gtgaaaaaag taaaccgcga caacatctct ctggatctgg caacaacgc tgaagccgtg | 480 |
| atcctgcgcg aagatatgct gccgcgtgaa aacttccgcc ctggcgaccg cgttcgtggc | 540 |
| gtgctctatt ccgttcgccc ggaagcgcgt ggcgcgcaac tgttcgtcac tcgttccaag | 600 |
| ccggaaatgc tgatcgaact gttccgtatt gaagtgccag aaatcggcga agaagtgatt | 660 |
| gaaattaaag cagcggctcg cgatccgggt tctcgtgcga aaatcgcggt gaaaaccaac | 720 |
| gataaacgta tcgatccggt aggtgcttgc gtaggtatgc gtggcgcgcg tgttcaggcg | 780 |
| gtgtctactg aactgggtgg cgagcgtatc gatatcgtcc tgtgggatga taacccggcg | 840 |
| cagttcgtga ttaacgcaat ggcaccggca gacgttgctt ctatcgtggt ggatgaagat | 900 |
| aaacacacca tggacatcgc cgttgaagcc ggtaatctgg cgcaggcgat tggccgtaac | 960 |
| ggtcagaacg tgcgtctggc ttcgcaactg agcggttggg aactcaacgt gatgaccgtt | 1020 |
| gacgacctgc aagctaagca tcaggcggaa gcgcacgcag cgatcgacac cttcaccaaa | 1080 |
| tatctcgaca tcgacgaaga cttcgcgact gttctggtag aagaaggctt ctcgacgctg | 1140 |
| gaagaattgg cctatgtgcc gatgaaagag ctgttggaaa tcgaaggcct tgatgagccg | 1200 |
| accgttgaag cactgcgcga gcgtgctaaa aatgcactgg ccaccattgc acaggcccag | 1260 |
| gaagaaagcc tcggtgataa caaaccggct gacgatctgc tgaaccttga aggggtagat | 1320 |
| cgtgatttgg cattcaaact ggccgcccgt ggcgtttgta cgctggaaga tctcgccgaa | 1380 |
| cagggcattg atgatctggc tgatatcgaa gggttgaccg acgaaaaagc cggagcactg | 1440 |
| attatggctg cccgtaatat ttgctggttc ggtgacgaag cg | 1482 |

<210> SEQ ID NO 5
<211> LENGTH: 801
<212> TYPE: DNA
<213> ORGANISM: Homo sapiens

<400> SEQUENCE: 5

| | |
|---|---|
| attgaattta cagaacaaac ggcgccgaaa attttcggcg gtgagattaa aacacatatc | 60 |
| ctgctgtttc tgccgaagag cgtttctgat tacgatggta aactgagtaa ttttaaaacc | 120 |
| gccgcagaat ctttcaaagg taagattctg ttcattttca ttgatagcga ccacacggac | 180 |
| aatcagcgta tcctggagtt cttttggtctg aagaagagg aatgcccggc tgtgcgtctg | 240 |
| attacgctgg aagaggaaat gacaaagtac aagccggaga gcgaggaact gactgcagaa | 300 |
| cgtatcaccg aattttgtca tcgtttcctg gaggggaaga ttaagccgca tctgatgagc | 360 |
| caggaactgc cggaggattg ggacaaacag ccagtgaaaa ttctggtggg gaagaattttt | 420 |
| gaagatgtgg ccttcgatga agaagaat gtgtttgtgg agttctacgc cccgtggtgt | 480 |
| gggcactgta acagctggc gccgatctgg gacaaactgg cgaaacgta taaagatcac | 540 |
| gaaaatattg tgatcgcgaa aatggattct accgcgaatg aagtagaagc ggtaaaagta | 600 |
| cactcttttc cgacgctgaa attctttcca gcgagcgcgg atcgtactgt cattgattat | 660 |
| aatggcgaac gtactctgga cggctttaag aaatttctgg aaagcggcgg ccaggatggc | 720 |
| gcgggcgatg atgatgacct ggaagacctg gaagaagcgg aggaaccaga catggaggag | 780 |
| gatgacgacc agaaagcggt c | 801 |

<210> SEQ ID NO 6
<211> LENGTH: 1461
<212> TYPE: DNA
<213> ORGANISM: Homo sapiens

<400> SEQUENCE: 6

```
gacgcaccgg aagaagagga tcatgtcctg gttctgcgca aaagcaactt cgcggaagca      60
ctggccgcac ataaatatct gctggtggaa ttttatgctc cttggtgcgg tcattgcaaa     120
gccctggccc cggagtacgc caaagccgca ggtaaactga agctgaagg tagcgaaatc      180
cgcctggcaa aggttgatgc tacggaagag agtgacctgg cgcagcagta tggtgtccgc     240
ggctatccta caattaaatt cttccgtaac ggtgataccg catctccaaa agaatatacc     300
gctggtcgcg aggcggacga tattgttaac tggctgaaga aacgcactgg ccctgccgca     360
accaccctgc tgatggcgc tgctgccgaa agcctggtcg aaagtagcga agttgccgtc      420
attggttct ttaaggatgt agaatctgac agtgccaaac agtttctgca agcggcagag      480
gctatcgatg acatcccgtt cggcatcacc tctaacagtg acgtattcag taaataccaa     540
ctggataaag acggcgttgt gctgttcaag aaatttgatg aaggtcgcaa caactttgag     600
ggtgaggtga ccaaggagaa cctgctggat tttattaagc acaaccaact gccgctggtt     660
attgaattta cagaacaaac ggcgccgaaa attttcggcg gtgagattaa acacatatc     720
ctgctgtttc tgccgaagag cgtttctgat tacgatggta aactgagtaa ttttaaaacc     780
gccgcagaat ctttcaaagg taagattctg ttcattttca ttgatagcga ccacacggac     840
aatcagcgta tcctggagtt cttggtctg aagaaagagg aatgcccggc tgtgcgtctg     900
attacgctgg aagaggaaat gacaaagtac aagccggaga gcgaggaact gactgcagaa     960
cgtatcaccg aattttgtca tcgtttcctg gaggggaaga ttaagccgca tctgatgagc    1020
caggaactgc cggaggattg ggacaaacag ccagtgaaag ttctggtggg gaagaatttt    1080
gaagatgtgg ccttcgatga agaagaat gtgtttgtgg agttctacgc cccgtggtgt     1140
gggcactgta acagctggc gccgatctgg gacaaactgg cgaaacgta taaagatcac     1200
gaaaatattg tgatcgcgaa aatggattct accgcgaatg aagtagaagc ggtaaaagta    1260
cactctttc cgacgctgaa attctttcca gcgagcgcgg atcgtactgt cattgattat    1320
aatggcgaac gtactctgga cggctttaag aaatttctgg aaagcggcgg ccaggatggc   1380
gcgggcgatg atgatgacct ggaagacctg gaagaagcgg aggaaccaga catggaggag    1440
gatgacgacc agaaagcggt c                                             1461

<210> SEQ ID NO 7
<211> LENGTH: 175
<212> TYPE: PRT
<213> ORGANISM: Homo sapiens

<400> SEQUENCE: 7

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110
```

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 8
<211> LENGTH: 176
<212> TYPE: PRT
<213> ORGANISM: Homo sapiens

<400> SEQUENCE: 8

Gly Met Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 9
<211> LENGTH: 31
<212> TYPE: DNA
<213> ORGANISM: Artificial Sequence
<220> FEATURE:
<223> OTHER INFORMATION: attB1

<400> SEQUENCE: 9
ggggacaagt ttgtacaaaa aagcaggctt c                                  31

<210> SEQ ID NO 10
<211> LENGTH: 525
<212> TYPE: DNA
<213> ORGANISM: Homo sapiens

<400> SEQUENCE: 10 atgacccgc tgggcccggc gtcttctctg ccgcaatcgt tcctgctgaa atgcctggaa    60
caggttcgta agattcaagg cgatggtgcg gccctgcagg aaaaactgtg cgccacctat   120
aagctgtgtc atccggaaga actggtcctg ctgggtcaca gcctgggtat cccgtgggca   180

```
ccgctgagct cttgcccgtc tcaggccctg caactggcag gctgtctgag tcagctgcat    240
tccggcctgt ttctgtacca gggtctgctg caagcgctgg aaggcattag tccggaactg    300
ggtccgaccc tggacacgct gcagctggat gtggctgact tcgcgaccac gatctggcag    360
caaatggaag aactgggtat ggcaccggct ctgcagccga cgcaaggtgc tatgccggcg    420
tttgcatccg cattccagcg tcgcgctggc ggtgtgctgg ttgcgtcaca tctgcaatcg    480
tttctggaag tcagctatcg tgtgctgcgc cacctggccc agccg                    525
```